United States Patent [19]
Hargest

[11] Patent Number: 5,441,477
[45] Date of Patent: Aug. 15, 1995

[54] METHOD AND APPARATUS FOR TREATING A PATIENT BY ELECTRO/FLUIDIZED BED THERAPY

[76] Inventor: Thomas S. Hargest, P.O. Box 21118, Charleston, S.C. 29413

[21] Appl. No.: 808,203
[22] Filed: Dec. 13, 1991
[51] Int. Cl.$^6$ ............................................. A61F 7/00
[52] U.S. Cl. ..................................... 601/16; 601/15; 607/98; 607/104
[58] Field of Search ................. 128/24, 24.1, 400, 399, 128/376, 419, 421, 422

[56] References Cited

U.S. PATENT DOCUMENTS

| | | | |
|---|---|---|---|
| 533,791 | 2/1895 | Doehring | 128/369 |
| 668,661 | 2/1901 | Schneider | 128/369 |
| 1,636,568 | 7/1927 | Kennedy | 128/400 |
| 2,956,565 | 10/1960 | Anderson | 128/369 |
| 3,760,800 | 9/1973 | Staffin et al. | 128/38 X |
| 3,866,606 | 2/1975 | Hargest | 128/71 |
| 4,214,576 | 7/1980 | Henley | 128/24.1 |
| 4,240,437 | 12/1980 | Church | 128/420 |
| 4,411,268 | 10/1983 | Cox | 128/421 |
| 4,481,686 | 11/1984 | La Coste | 128/38 X |
| 4,498,462 | 2/1985 | Henley | 128/65 X |
| 4,583,530 | 4/1986 | Henley | 128/65 |
| 4,642,825 | 2/1987 | Kurita | 128/400 X |
| 4,648,392 | 3/1987 | Cartier et al. | 128/160 |
| 4,960,124 | 10/1990 | Masaki | 128/421 |
| 4,976,264 | 12/1990 | Petrofsky | 128/421 |
| 5,063,910 | 11/1991 | Cartier | 128/65 X |

FOREIGN PATENT DOCUMENTS 332242A 9/1989 European Pat. Off. .

*Primary Examiner*—Robert A. Hafer
*Assistant Examiner*—Brian E. Hanlon
*Attorney, Agent, or Firm*—Luke J. Wilburn, Jr.

[57] ABSTRACT

Method and apparatus for treating a patient by electrotherapy and fluidized bed thermal therapy. A body portion of a patient is submerged in a fluidizable bed of solid particles, and the bed is selectively fluidized and de-fluidized as desired while controlling the temperature of the bed of solid particles. Electrotherapy treatment is applied to the portion of the body of the patient submerged in the bed of solid particles through electrodes attached to the body part which are connected to an electrical generator which produces radio frequency signals in continuous or modulated modes. The electrotherapy and fluidized bed thermal therapy may be applied consecutively or concurrently to the body part for treatment thereof.

9 Claims, 1 Drawing Sheet

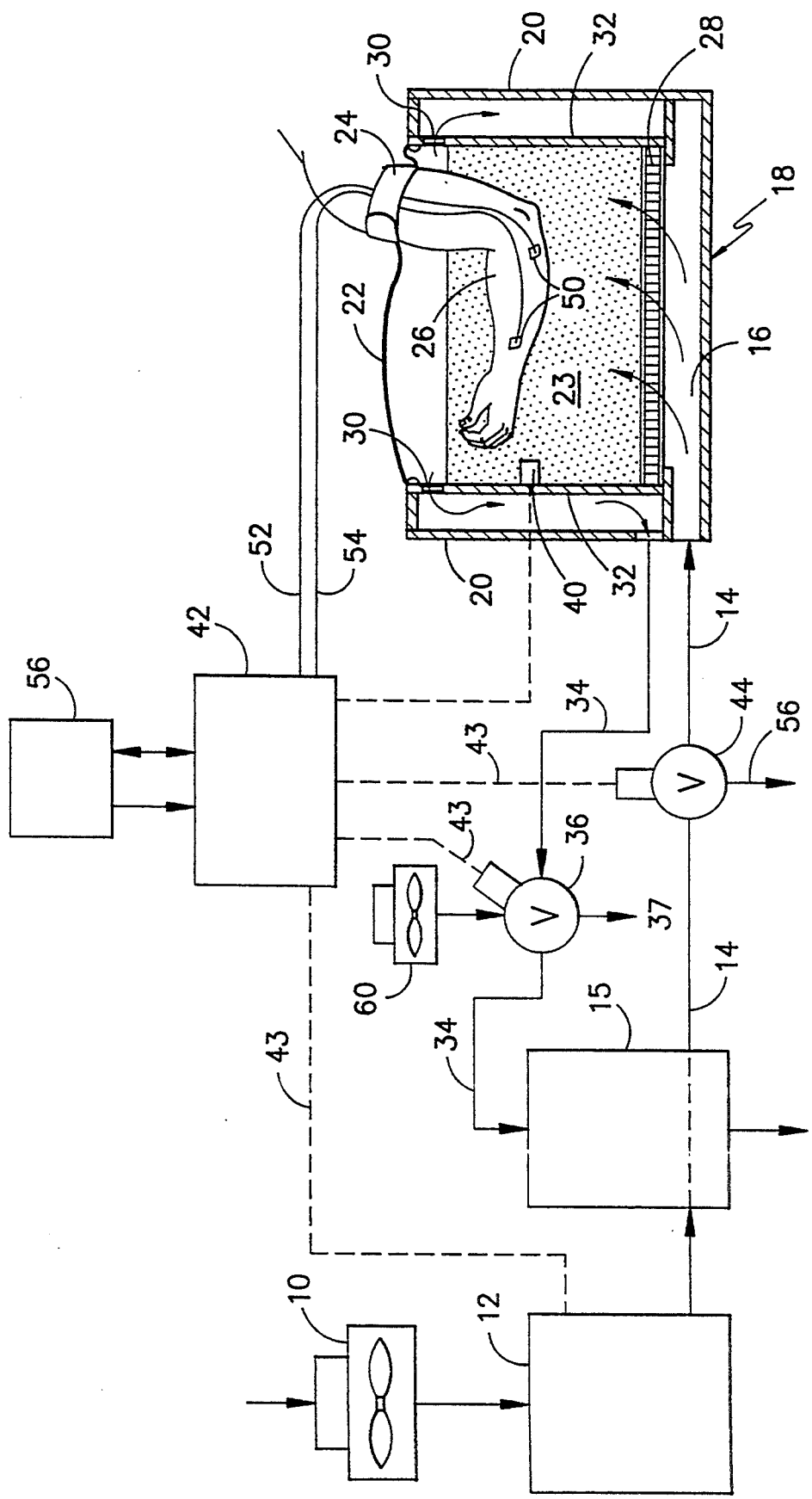
FIG. -1-

METHOD AND APPARATUS FOR TREATING A PATIENT BY ELECTRO/FLUIDIZED BED THERAPY

This invention relates to method and apparatus for treating a patient by combined application of electrotherapy and a thermally controlled fluidizable particulate material, and, more particularly to method and apparatus for providing both electrotherapy treatment and temperature controlled, fluidizable particulate material treatment of a portion of the body of a patient.

BACKGROUND OF THE INVENTION

Electrotherapy devices have been used for treatment of the human body to reduce pain, muscle spasm, edema, and muscle re-education. Typically, such devices employ an electrical generator or generators which produce a radio frequency sinusoidal current in continuous or modulated modes. The current output of the generators is applied through electrodes attached to the skin of a body portion of a patient to electrically stimulate the body portion.

Very early U.S. Pat. Nos. 533,791 and 668,661 disclose apparatus for subjecting a patient to direct electrical current traveling from a metal plate, or conductor, located below and above the patient, with the conductivity of the skin surface enhanced by packing sand, metal, shot, or salt crystals around the patient. The sand may be heated with steam or hot air which causes the patient to sweat, providing a conductive path for the electrical current. It is believed that such treatment by direct current with a positive charge to a negative charge through the patient's body, as disclosed in these early patents, could be quite dangerous and could cause burns and serious injury.

More recent U.S. Pat. Nos. 4,411,268; 4,960,124; and 4,976,264 disclose electrotherapy devices for muscle stimulation of the human body wherein generated electrical stimulation signals are applied to a patient's body through electrodes attached to the body. U.S. Pat. No 4,240,437 discloses apparatus for electric massage treatment of animals, including humans, wherein pulse repetition rate, amplitude, and polarity of the electrical signals can be controlled for selected periods of time.

It is also known to treat portions of the human body by the use of a fluidized bed of solid particles suspended in air in such a manner that the mixture possesses the property of a fluid which may be heated or cooled to provide a massaging action to the portion of the body submerged in the fluidized bed. U.S. Pat. No. 4,498,462 discloses apparatus for applying massage and heat or cold therapy to the arms, legs, or other parts of the body of a human or animal using a fluidized solids bed as the heat transfer medium. The massaging action of the fluidized bed may be accompanied by heat or cold imparted to the mass by utilizing suitable heating elements, or heating may be generated by compressing the gas employed to fluidize the bed. U.S. Pat. No. 4,583,530 discloses a fluidized bed apparatus for treating equine body parts, and discusses the use of such fluidized beds for whirlpool massaging action for treatment of arms, legs, and other body parts of a human.

U.S. Pat. No. 4,648,392 discloses a vertical cylindrical vessel containing a flexible tubular bag into which a limb of the human body may be inserted. The vessel contains granular molding material which may be fluidized by air and surrounds an inner and outer bag containing the body limb. The space between the bags is filled with mercury to treat oedema of the upper and lower extremities of the human body. The fluidized bed is de-fluidized to achieve a solid molding surrounding the mercury-filled space and limb of the patient.

U.S. Pat. No. 3,866,606 discloses apparatus and method for cyclically forming a precisely contoured support for a patient requiring a fixed position, as for example, undergoing traction, by means of periodically fluidizing granular material disposed within a container which, upon successive fluidization, forms the contoured support to distribute pressure over a substantial portion of the body of a patient in avoidance of concentrated pressure on restricted areas thereof.

European Patent Application 332,242-A discloses use of a bed of moisture and fluid absorbing beads which are fluidized by an air supply having low relative humidity and suitable temperature to increase the regenerative action of the fluidization bed necessary for abstracting moisture and fluid from industrial and agricultural products, humans, and animals.

Although electrotherapy treatment and fluidized bed massage treatment have heretofore been employed separately in treatment of human patients, it not known that such temperature controlled massage treatment and electrotherapy have been simultaneously employed in treatment of a patient in varying sequences to produce a combined therapy.

BRIEF OBJECTS OF THE PRESENT INVENTION

It is an object of the present invention to provide method and apparatus for treating a patient by combined application of electrotherapy and a thermally controlled fluidizable particulate material.

It is another object to provide method and apparatus for treatment of a portion of the body of a human patient by electrotherapy and by application of a temperature controlled fluidizable particulate material.

It is a more specific object to provide method and apparatus for treatment of a portion of the body of a human patient by concurrent application of electrotherapy and of a temperature controlled fluidizable particulate material while varying the duration and extent of application of the electrotherapy pulses, temperature, and fluidization of the fluidized bed.

SUMMARY OF THE INVENTION

The present method and apparatus comprises a fluidizable bed of electrically non-conductive solid particulate material which may be maintained in a fluidized state or in a defluidized state to deliver heat or cold therapy to a portion of the body of a patient submerged in the material. In combination with such thermal therapy provided by the fluidizable bed, the method and apparatus of the present invention provide electrotherapy treatment by application of a radio frequency current directly to an area of the portion of the body of a patient in the fluidizable bed, utilizing an electronic therapy device of a type known in the art. Because the mass of the solid particles comprising the fluidizable bed is non-conductive, electrotherapy treatment may be applied to and carried out on the body portion of the patient submerged in the bed without fear of electrical shock or injury due to conductivity of the bed.

In thermal treatment of the body portion submerged in the fluidizable bed, heat or cold therapy may be transferred to the body of a patient by conduction when the bed is in a defluidized state to provide concentrated application of heat or cold to the body portion. When the thermal treatment is applied during fluidization of the bed, the heat or cold is transferred by convection to the body part, providing a more dispersed and less intense concentration of the thermal therapy.

BRIEF DESCRIPTION OF THE DRAWING

The above as well as other objects of the present invention will become more apparant and the invention will be better understood from the following detailed description of preferred embodiments of the same, when taken together with the accompanying drawing, in which:

FIG. 1 is a schematic block diagram illustration and vertical sectional elevation view of apparatus of the present invention for practice of the method of the present invention wherein a part of the body of a human patient, e.g., an arm, is submerged in a fluidized mass of particulate material, and electrodes are attached to the body of the patient for simultaneous application of electrotherapy and thermally controlled fluidized bed therapy to the submerged body part of the patient.

DETAILED DESCRIPTION OF PREFERRED EMBODIMENTS OF THE INVENTION

As seen in FIG. 1, air is supplied from a pressurized air source, such as a fan or blower 10, to a thermal energy unit, such as a heat pump 12, which heats or cools the air passing therethrough to a desired temperature. The thermally treated air under pressure passes, in the directions indicated by the arrows, from heat pump 12 by way of an air supply conduit 14 through a heat exchanger unit 15 into a pressurized air compartment 16 located in the lower portion of an insulated tank 18. Tank 18 is shown in a vertical sectional elevation view.

Tank 18, which suitably may be of rectangular horizontal cross-section, has upstanding outside walls 20 and an open top which is closed by an air impervious flexible sheet, or cover, 22. Located within the tank beneath the cover is a fluidizable bed of particulate material, such as glass beads 23. The beads are electrically non-conductive and may be made of optical soda lime glass coated with silicone or polytetrafluoroethylene to prevent clumping, and typically may be in a size range of between about 50 to 150 microns in diameter. Pure soda lime glass is desirable since there is no free silica, lead, or other metals present in the fluidizable bed.

Tank cover 22 is provided with an adjustable cuff 24 having an opening for closely encircling a portion of the body of a human patient, such as an arm 26, which is inserted through the cuff and submerged in the fluidizable bed of glass beads. Pressurized air in tank compartment 16 passes upwardly through an air pervious, horizontal diffuser plate 28 and into the bed of glass beads 23 to fluidize the same. Air leaving the fluidized bed passes through a screened air intake opening 30 located along the upper portion of inner side walls 32 of tank 18. Air between the walls 32, 20 of the tank may be directed by an exit air conduit 34 and suitable valve means, such as a solenoid-operated valve 36, alternatively to discharge from the system through a discharge line 37, or to pass across heat exchange unit 15 located in the air supply conduit 14 from heat pump 12.

A temperature sensing device 40 located in the fluidizable bed of beads 23 in tank 18 is electrically connected to a suitable master control box 42. Also operatively electrically connected to control box 42 is an electrotherapy unit 56 of commercially available type. Output signals from control box 42 are electrically connected by suitable lines 43 to operate heat pump 12 and suitable solenoid valves 44 and 36 located in the respective air supply and return conduits 14, 34, as will be explained.

As seen in FIG. 1, electrodes 50 attached to selected portions of a patient's arm 26 submerged in the fluidizable bed are operatively connected by electrical lead wires 52, 54 through master control box 42 to the electrotherapy unit 56. Control box 42 contains conventional, commercially available control means for operating both the fluidizable bed thermal treatment and the electrotherapy treatment components of the invention. Programmable means, such as a conventional microprocessor known in the art, may be located-in control box 42 and programmed to operate the fluidizable bed and electrotherapy device in various sequences of operation, either individually or simultaneously, to treat the submerged body portion of the patient. Control may also be accomplished manually from control box 42 to operate heat pump 12 and valves 36 and 44.

The fluidizable bed of particulate material may be fluidized and de-fluidized in varying sequences to provide desired thermal treatment to the body portion of a patient. The temperature of the bed may be maintained at a desired thermal level of heating or cooling through temperature sensing device 40 and control box control means to impart both conductive and convective thermal energy to the body part. If conductive heating or cooling of the body part is desired, the thermally treated incoming air may be removed from the air circulating system by discharging all or a sufficient portion of the same through solenoid valve 44 and discharge conduit 56 to maintain the bed in a de-fluidized state. If convective heating or cooling of the body part is desired, pressurized air is directed by valve 44 to maintain the air at the desired pressure to fluidize the bed.

To facilitate heating or cooling of the incoming air to the fluidized bed, return air (either heated or cooled) from tank 18 may be passed through conduit 34 and heat exchanger 15 in heat exchange relationship with the incoming air from the heat pump 12. If desired, return air from tank 18 may be discharged from the system by valve 36 through discharge conduit 37.

If desired, to facilitate the time in changing the temperature of incoming air from the heat pump 12, room air may be supplied across the heat exchanger 15 by air blower 60 and valve 36.

In like manner, the control means in box 42 may be operated to provide electrotherapy energy pulses from the electrotherapy unit 56 to the electrodes 50 in continuous or discontinuous manner, and at varying levels of electrical intensity, as desired.

As indicated, electrotherapy/fluidizable bed thermal treatment of the patient may be controlled and operated by program means or manually at control box 42 to provide various sequences of treatments. The thermal fluidizable bed treatment and the electrotherapy treatment may be applied individually, consecutively, or concurrently to the body part of the patient submerged in the fluidizable bed. The control means may be operated to provide continuous or intermittent thermal heating or cooling. The temperature of the air and bed for heating or cooling the body part is accomplished by regulation of the heat pump unit 12 and valves 36, 44 in response to temperature sensing device 40. Convective thermal treatment of the body part occurs when the bed is in a fluidized state by passage of thermally treated air under sufficient pressure through the tank and bed. Conductive thermal treatment of the body part is accomplished by de-fluidizing the bed by discharging the thermally treated air from the system through valve 44 and discharge conduit 56.

Various commercially available electrotherapy units may be employed in carrying out the present invention. One such device may consist of a medium frequency current generator sold under the trademark "Omnistim" by Physio Technology, Inc. of Topeka, Kans. The electrotherapy signals from the electrotherapy unit also may be controlled manually or by program means in master control box 42 to deliver continuous or intermittent electrical stimulation to the body part submerged in the bed, at varying frequencies, as desired.

That which is claimed is:

1. A method of treating a patient by combined application of electrotherapy and a thermally controlled fluidizable particulate material comprising the steps
    (a) creating a fluidizable bed of solid particles,
    (b) submerging at least a portion of the body of a patient in the bed of solid particles,
    (c) selectively fluidizing and de-fluidizing the bed of solid particles, as desired, while controlling the temperature of the bed of solid particles, and
    (d) selectively applying electrotherapy treatment to the portion of the body of the patient submerged in the bed of solid particles.

2. A method as defined in claim 1 wherein the fluidizable bed is de-fluidized and the temperature of the bed is controlled to provide conductive heat treatment to the portion of the body submerged therein.

3. A method as defined in claim 1 wherein the fluidizable bed is de-fluidized and the temperature of the bed is controlled to provide conductive cooling treatment to the portion of the body submerged therein.

4. A method as defined in claim 1 wherein the fluidizable bed is fluidized and the temperature of the bed is controlled to provide convective heat treatment to the portion of the body of the patient submerged therein.

5. A method as defined in claim 1 wherein the fluidizable bed is fluidized and the temperature of the bed is controlled to provide convective cooling treatment to the portion of the body of the patient submerged therein.

6. A method as defined in claim 1 wherein the electrotherapy is selectively applied to the portion of the body submerged in the bed by attaching electrodes to the portion of the body submerged in the bed of solid particles and providing an electrical frequency through the electrodes to treat a portion of the body submerged in the bed of solid particles.

7. A method as defined in claim 1 wherein steps (c) and (d) thereof are performed simultaneously on the portion of the body of the patient submerged in the bed of solid particles.

8. Apparatus for treating a patient by combined application of electrotherapy and a thermally controlled fluidizable particulate material comprising
    (a) means for creating a fluidizable bed of solid particles for submerging at least a portion of the body of a patient therein,
    (b) means for selectively fluidizing and de-fluidizing the bed of solid particles, as desired, while controlling the temperature of the bed of solid particles, and
    (c) means for selectively applying electrotherapy treatment to the portion of the body of the patient submerged in the bed of solid particles.

9. Apparatus as defined in claim 8 wherein said means for creating a fluidizable bed of solid particles comprises a container of solid particles having an opening for the insertion of at least a portion of the body of a patient therein, said means for selectively fluidizing and de-fluidizing the bed comprises means for supplying a stream of temperature-controlled air to the bed of solid particles at selected intervals, and said means for selectively applying the electrotherapy treatment to the portion of the body of the patient submerged in the bed comprises means providing a source of variable frequency energy, and electrodes connected to said means providing said source and extending into the bed of solid particles for attachment to the portion of the body of the, patient submerged in the bed.

* * * * *

UNITED STATES PATENT AND TRADEMARK OFFICE
CERTIFICATE OF CORRECTION

PATENT NO. : 5,441,477

DATED : August 15, 1995

INVENTOR(S) : Thomas S. Hargest

It is certified that error appears in the above-identified patent and that said Letters Patent is hereby corrected as shown below:

In column 4, line 17, after "located", delete "-".

In column 5, line 21, claim 1, after "steps", add --of--.

In column 6, line 42, after "the", second occurrence, delete ",".

Signed and Sealed this

Thirty-first Day of October 1995

Attest:

BRUCE LEHMAN

*Attesting Officer*  Commissioner of Patents and Trademarks